(12) United States Patent
Wang et al.

(10) Patent No.: US 9,890,352 B2
(45) Date of Patent: Feb. 13, 2018

(54) INJECTABLE TISSUE ENGINEERED CARTILAGE IN VITRO CONSTRUCTION APPARATUS

(71) Applicant: FIRST AFFILIATED HOSPITAL, THIRD MILITARY MEDICAL UNIVERSITY, CHINESE PEOPLE'S LIBERATION ARMY, P.R. CHINA, Chongqing (CN)

(72) Inventors: Fuyou Wang, Chongqing (CN); Junli Liu, Chongqing (CN); Liu Yang, Chongqing (CN); Ying Zhang, Chongqing (CN); Guangxing Chen, Chongqing (CN); Lin Guo, Chongqing (CN); Xiaojun Duan, Chongqing (CN)

(73) Assignee: FIRST AFFILIATED HOSPITAL, THIRD MILITARY MEDICAL UNIVERSITY, CHINESE PEOPLE'S LIBERATION ARMY, P.R. CHINA, Chongqing (CN)

( * ) Notice: Subject to any disclaimer, the term of this patent is extended or adjusted under 35 U.S.C. 154(b) by 193 days.

(21) Appl. No.: 14/907,621

(22) PCT Filed: Jul. 21, 2014

(86) PCT No.: PCT/CN2014/082599
§ 371 (c)(1),
(2) Date: Jan. 26, 2016

(87) PCT Pub. No.: WO2015/010585
PCT Pub. Date: Jan. 29, 2015

(65) Prior Publication Data
US 2016/0160162 A1  Jun. 9, 2016

(30) Foreign Application Priority Data
Jul. 26, 2013  (CN) .......................... 2013 1 0320174

(51) Int. Cl.
*C12M 1/36* (2006.01)
*C12M 1/38* (2006.01)
(Continued)

(52) U.S. Cl.
CPC ........... *C12M 21/08* (2013.01); *A61F 2/3094* (2013.01); *A61L 27/38* (2013.01); *B65D 85/50* (2013.01);
(Continued)

(58) Field of Classification Search
CPC .. A61L 2430/06; A61L 2430/10; A61L 27/38; A61L 27/3604; A61L 27/3637;
(Continued)

(56) References Cited

U.S. PATENT DOCUMENTS

2007/0248575 A1   10/2007  Connor et al.
2009/0104698 A1*   4/2009  Dutra ..................... C12M 33/12
                                                              435/378

FOREIGN PATENT DOCUMENTS

CN     1838997 A     9/2006
CN     1950041 A     9/2006
(Continued)

OTHER PUBLICATIONS

International Search Report for corresponding International Patent Application No. PCT/CN2014/082599 dated Oct. 27, 2014.

*Primary Examiner* — William H Beisner
*Assistant Examiner* — Lydia Edwards
(74) *Attorney, Agent, or Firm* — Merchant & Gould P.C.

(57) ABSTRACT

An injectable tissue engineered cartilage in vitro construction apparatus, comprising an incubator (1), a centrifugal device arranged in the incubator (1), and a control system for controlling a temperature in the incubator (1) and an action of the centrifugal device. The centrifugal device comprises a centrifuge, a container base (2) mounted onto the centri-
(Continued)

fuge, a dosing system for adding preparation reagent, and a stirring system for stirring the reagent. With a controller (17) and a pH sensor (16), a measured pH value will be transmitted by the pH sensor (16) to the controller (17) in real time. The controller (17) controls an action of a driving mechanism via a control module II (21), to drive a piston rod to add NaOH solution into a container tank (6). When the pH value of the solution falls in a predetermined range, the driving mechanism is stopped, to precisely control the pH value of the solution. With the stirring system and the centrifugal device, the solution can be stirred and centrifuged as desired, to eventually in vitro construct an injectable tissue engineered cartilage. This relief the burden of the medical staff and improve production efficiency.

7 Claims, 2 Drawing Sheets

(51) Int. Cl.
| | | |
|---|---|---|
| *C12M 3/00* | (2006.01) | |
| *A61F 2/30* | (2006.01) | |
| *A61L 27/38* | (2006.01) | |
| *C12M 1/34* | (2006.01) | |
| *C12M 1/00* | (2006.01) | |
| *B65D 85/50* | (2006.01) | |
| *C12M 1/06* | (2006.01) | |
| *C12M 3/04* | (2006.01) | |

(52) U.S. Cl.
CPC .......... *C12M 27/02* (2013.01); *C12M 27/10* (2013.01); *C12M 41/12* (2013.01); *C12M 41/14* (2013.01); *C12M 47/02* (2013.01); *A61L 2430/06* (2013.01)

(58) Field of Classification Search
CPC ....... B65D 85/50; C12M 21/08; C12M 27/02; C12M 27/10; C12M 41/12; C12M 41/26; C12M 41/48; C12M 41/14; C12M 47/02
USPC ...................................................... 435/286.1
See application file for complete search history.

(56) References Cited

FOREIGN PATENT DOCUMENTS

| CN | 102672875 A | 9/2012 |
|---|---|---|
| CN | 103357069 A | 10/2013 |
| CN | 203370139 U | 1/2014 |
| EP | 2007196 A2 | 12/2008 |

\* cited by examiner

INJECTABLE TISSUE ENGINEERED CARTILAGE IN VITRO CONSTRUCTION APPARATUS

This application is a National Stage Application of PCT/CN2014/082599, filed 21 Jul. 2014, which claims benefit of Serial No. 201310320174.1, filed 26 Jul. 2013 in China and which applications are incorporated herein by reference. A claim of priority is made to each of the above disclosed applications.

FIELD OF INVENTION

The present invention relates to an apparatus to construct cartilage in vitro by using type II collagen. In particular, the present invention relates to an injectable tissue engineered cartilage in vitro construction apparatus. The prepared injectable tissue-engineered cartilage is mainly used for treatment of cartilage injuries.

BACKGROUND

The cartilage defects at joints caused by trauma or osteopathia are common clinical diseases, which severely affect the life quality of the patients, and have become one of the main reasons of physical disabilities. In US, the incidence rate is 1.5‰-3‰; while in China, the incidence rate is about 5-6 times of US and is rising gradually year by year. Joint cartilage belongs to hyaline cartilage, which lacks of neurovascular nutrition and is hard to self-heal. Current clinical treatment measures all have substantial deficiencies. For instance, conservative therapy and joint debridement can only temporarily relief the pain, but cannot stop the disease progress. Autologous osteochondral transplantation can lead to donor site damage, and has difficulty to repair larger area defect due to limited source. Allograft osteochondral transplantation may have the possibility of immunological rejection and disease spreading. Artificial joint replacement is rather expensive, may lead to more complications, has higher revision rate, and especially has big physical and mental effects and heavy financial burden on the young patients.

Emerge and rapid development of tissue engineering provide a new technology for regenerative repair of joint cartilage. Three-dimensional scaffold provided by tissue engineering scaffold material for constructing cell of the tissue facilitates cell adhesion, cell proliferation and cell differentiation, which provides suitable external environment for cell growth. In tissue engineering, the scaffold material acts as extracellular matrix, and simulates structure and function of extracellular matrix. The scaffold material not only provides support to keep the shape of original tissue, but also acts as a template to provide a site for cells to board, grow, differentiate and proliferate, so as to guide the impaired tissues to regenerate and to control structure of the regenerated tissues.

The prepared type II collagen, upon mixed with hydrochloric acid solution, will be sealed and packaged for store. When needed, the type II collagen-hydrochloric acid solution is first to be neutralized, and then the prepared BMSCs will be moved into the type II collagen-hydrochloric acid solution, which upon fully mixed, centrifuged to remove bubbles, will be suctioned into a vacuum needle for use. Currently, there is no special in vitro construction apparatus for injectable tissue engineered cartilage available, and such apparatus is manually prepared by medical staff, which adds burden to the medical staff. Further, the prepared injectable tissue engineered cartilage has low acceptability, causing unnecessary waste of material.

SUMMARY

In view of above, the present invention intends to provide an in vitro construction apparatus for injectable tissue engineered cartilage. The apparatus can perform in vitro construction of an injectable tissue engineered cartilage, so as to relief the burden of the medical staff and to improve efficiency.

In order to achieve the above objective, the present invention provides the following technical solutions:

An in vitro construction apparatus for injectable tissue engineered cartilage, comprising: an incubator, a centrifugal device arranged in the incubator, and a control system for controlling temperature in the incubator and action of the centrifugal device. The centrifugal device comprises a centrifuge, a container base mounted on the centrifuge, a dosing system for adding a preparation of reagents, and a stirring system for stirring the reagents.

The centrifuge comprises a bottom base and a plate fitted with the container base. The bottom base is arranged with a motor for rotating the plate thereon.

The container base is provided with a container tank. The stirring system comprises an upper base positioned above the container base. A stirring rod extends from the bottom surface of the upper base to align with the container tank. A driving device is arranged between the upper base and the bottom base for driving the upper base to move up and down.

The dosing system comprises a reagent tank positioned on the upper base for containing the preparation of reagent, a piston rod cooperated with the reagent tank, and a driving mechanism for driving the piston rod to move. A dosing channel is arranged between the reagent tank and the container tank, with a control valve I thereon.

The container base has a receiving device therein, which includes an aseptic injector fixed in the container base. A receiving channel is arranged between the aseptic injector and the container tank, with a control valve II thereon.

The container tank has a PH sensor for detecting PH value of the reagent.

The control system comprises a controller, a timer/timers connected with the controller for counting time, a temperature sensor for measuring the temperature in the incubator, a motor drive circuit for controlling motor action, a control module I for controlling lifting action of the driving device and a control module II for controlling the driving mechanism action. The incubator has a temperature control output system therein. The controller connects with the PH sensor, the control valve I, the control valve II and the temperature control output system, respectively. The controller receives a signal representing PH value of the reagent measured by the PH sensor and sends a control command to the control module II and the control valve I.

Yet, the driving device comprises a guiding rod arranged between the upper base and the bottom base, and a cylinder for driving the guiding rod to have fore and aft motion. The cylinder has an electromagnetic directional valve on its gas path, and the control module I is connected with the electromagnetic directional valve.

Yet, the dosing channel includes dosing channel(s) I positioned on the upper base corresponding to respective reagent tanks and dosing channel(s) II arranged in the stirring rod and respectively connected with the dosing channel(s) I.

Yet, the control valve I is arranged on the dosing channel(s) I.

Yet, the driving mechanism comprises a servo motor, a screw rod that rotates under the drive of the servo motor and parallels to the piston rod, and a screw sleeve sleeved on the screw rod. The screw sleeve is fixedly connected with the piston rod. The control module II is connected with the servo motor.

Yet, the stirring rod has a stirring blade thereon.

Yet, the reagent tank has a displacement sensor for detecting position of the piston rod.

Technical Effects

The present invention provides an injectable tissue engineered cartilage in vitro construction apparatus. With the provided centrifugal device, the container base can be driven to achieve high speed centrifugal rotation under the action of the centrifuge. With the provided stirring system, the stirring rod will be inserted into the container tank when stirring is needed, and at the same time the centrifuge will be controlled to rotate at a low speed, to perform stirring. With the provided dosing system, the required reagent can be quantitatively added into the container tank during preparation, by having the required reagent in the reagent tank.

By providing the control system, the controller sends control command to the temperature control output system of the incubator with the temperature signal of the temperature sensor, so that the temperature in the incubator can always satisfy requirements of preparation. The motor drive circuit can control the motor to switch on/switch off, as well as the rotation rate and rotation time. The control module I controls the driving device to lift up and down, so as to stir the solution or centrifuge the solution if desired. The PH sensor will measure the PH value of the reagent and send such signal to the controller in real time. The controller controls the motion of the control valve I and controls the motion of the driving mechanism via the control module II, to add reagent into the container tank or stop adding reagent into the container tank, to ensure that the PH value of the reagent will eventually fall in a predetermined range, so as to precisely control the PH value.

In view of above, the injectable tissue engineered cartilage in vitro construction apparatus of the present invention can be able to automatically perform in vitro construction of the injectable tissue engineered cartilage, so as to relief the burden of the medical staff and to improve production efficiency. Also, the quality of the resulting injectable tissue engineered cartilage can be effectively guaranteed.

BRIEF DESCRIPTION OF THE DRAWINGS

In order to have the objective, the technical solutions and technical effects of the present invention more clear, detailed description is provided in connection with the drawings as follows.

Figure 1:
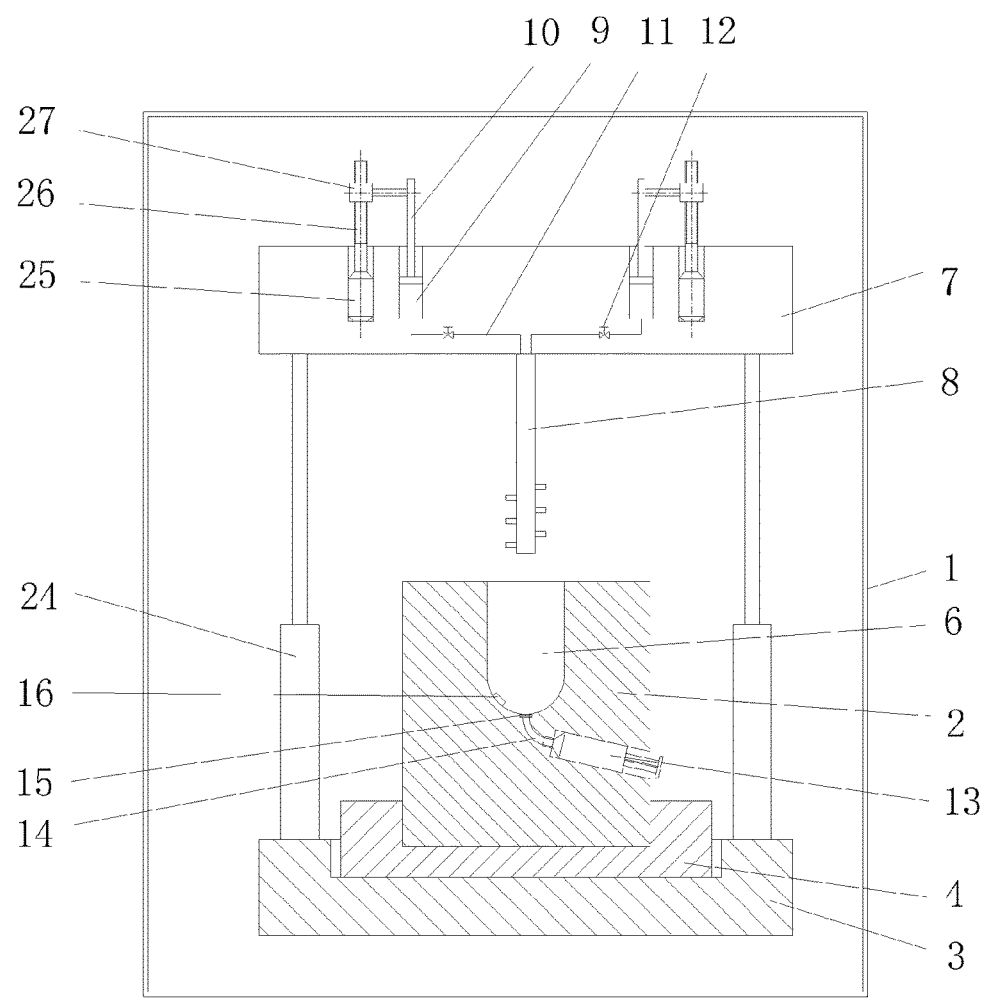
FIG. 1 is a schematic view of an in vitro construction apparatus for an injectable tissue engineered cartilage according to one embodiment of the present invention.
Figure 2:
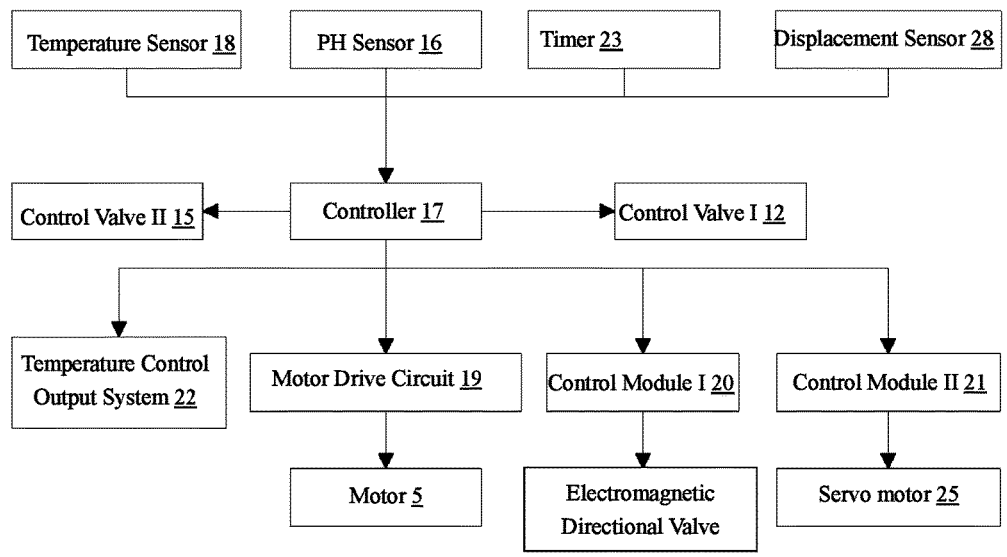
FIG. 2 is a block diagram to illustrate control principles.
Figure 3:
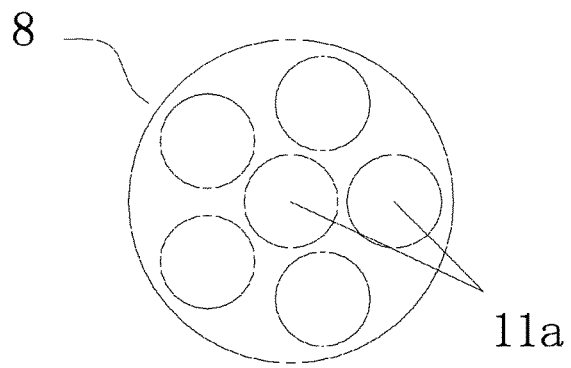
FIG. 3 is a cross sectional view of a stirring rod.

Reference numerals are listed as follows:

1—incubator; 2—container base; 3—bottom base; 4—plate; 5—motor, 6—container tank; 7—upper base; 8—stirring rod; 9—reagent tank; 10—piston rod; 11—dosing channel; 11a—dosing channel II; 12—control valve I; 13—aseptic injector; 14—receiving channel; 15—control valve II; 16—PH sensor; 17—controller; 18—temperature sensor; 19—motor drive circuit; 20—control module I; 21—control module II; 22—temperature control output system; 23—timer; 24—guiding rod; 25—servo motor, 26—screw rod; 27—screw sleeve, 28—displacement sensor.

DETAILED DESCRIPTION

In connection with the accompanying drawings, preferred embodiments will be described in detail.

FIG. 1 shows a schematic view of an in vitro construction apparatus for an injectable tissue engineered cartilage according to one embodiment of the present invention. In this embodiment, the in vitro construction apparatus for injectable tissue engineered cartilage comprises an incubator 1, a centrifugal device in the incubator 1, and a control system for controlling the temperature in the incubator 1 and motion of the centrifugal device. The centrifugal device includes a centrifuge, a container base 2 mounted on the centrifuge, a dosing system for adding a preparation of reagent(s), and a stirring system for stirring the reagent(s). The centrifuge comprises a bottom base 3 and a plate 4 fitted with the container base 2. The bottom base 3 is provided with a motor 5 for driving the plate 4 to rotate.

The container base 2 is provided with a container tank 6. The stirring system comprises an upper base 7 positioned above the container base 2. A stirring rod 8 that aligns with the container tank 6 extends from the upper base 7. A driving device is arranged between the upper base 7 and the bottom base 3 for driving the upper base 7 to move up and down. By driving the upper base 7 to move up and down, the stirring rod 8 can insert into or exit from the container tank 6. Preferably, the stirring rod 8 has a stirring blade, to enhance stirring effects.

The dosing system includes a reagent tank 9 positioned on the upper base 7 for containing preparation of reagents, a piston rod 10 cooperated with the reagent tank 9, and a driving mechanism for driving the piston rod 10 to move. A dosing channel 11 is arranged between the reagent tank 9 and the container tank 6, with a control valve I 12 thereon. By opening/closing the control valve I 12, reagents stored in different reagent tanks 9 can be added to the container tank 6. Further, by controlling the displacement distance of the piston rod 10, the amount of the reagents to be added can be precisely controlled.

The container base 3 has a receiving device therein, which includes an aseptic injector 13 fixedly mounted in the container base 3. A receiving channel 14 is provided between the aseptic injector 13 and the container tank 6, with a control valve II 15 thereon. When opening the control valve II 15, under centrifugal force, the reagents in the container tank 6 will be injected into the aseptic injector 13 for use via the receiving channel 14.

The container tank 6 has a PH sensor 16 therein, for detecting PH value of the reagents. With the PH sensor 16, the PH value of the reagents in the container tank 6 can be precisely measured, and a signal of the PH value will be fed back to the controller 17.

The control system comprises the controller 17, timer(s) 23 connected with the controller 17 for counting the time, a temperature sensor 18 for measuring the temperature in the incubator 1, a motor drive circuit 19 for controlling motion of the motor 5, a control module I 20 for controlling the driving device for lifting up and down, and a control module II 21 for controlling motion of the driving mechanism. The incubator 1 has a temperature control output system 22 therein. The controller 17 is connected with the PH sensor 16, the control valve I 12, the control valve II 15 and the temperature control output system 22, respectively. The controller 17 receives a signal of PH value of the reagents measured by the PH sensor 6 and sends a control command to the control module II 21 and the control valve I 12. The timer(s) 23 can control the motor 5 and the driving device the time for motion, so that the apparatus will act based on the preset time procedure.

The driving device of this embodiment comprises a guiding rod 24 arranged between the upper base 7 and the bottom base 3, and a cylinder used for driving the guiding rod 24 to have fore and aft motion. An electromagnetic directional valve is provided on a gas path of the cylinder. The control module I 20 is connected with the electromagnetic directional valve. By controlling the electromagnetic directional valve, the guiding rod 24 can drive the upper base 7 to move up and down.

The dosing channel 11 includes dosing channels I 11*a* in the upper base 7 corresponding to respective reagent tanks 9, and dosing channels II 11*a* in the stirring rod 8 and connected with the dosing channels I. Configuring the dosing channels II 11*a* in the stirring rod 8 can simplify the structure and can use the stirring rod 8 to add reagents into the container. Preferably, the control valve I 12 is disposed on the dosing channels I.

The driving mechanism comprises a servo motor 25, a screw rod 26 that rotates under driven by the servo motor 25 and in parallel to the piston rod 10, and a screw sleeve 27 sleeved onto the screw rod 26. The screw sleeve 27 is fixedly connected with the piston rod 10 via a connecting rod. The control module II 21 is connected with the servo motor 25. That is, the control module II 21 is a servo motor drive module. Controlling the servo motor 25 can drive the piston rod 10 to act and add reagents into the container tank 6. Preferably, a reagent tank 9 is provided with a displacement sensor 28 for detecting position of the piston rod 10. The displacement sensor 28 allows quantitative measurement of the amount of the reagents added into the container tank 6. Further, the displacement sensor 28, together with the PH sensor 16, can achieve a closed-loop control system for the servo motor 25.

The injectable tissue engineered cartilage in vitro construction apparatus of this embodiment has a centrifugal device. With the centrifuge, the container base 3 can be driven to have high speed centrifugal rotation. With the stirring system, the stirring rod 8 will insert into the container tank 6 when stirring is needed, and at the same time the centrifuge will be controlled to rotate at a low speed, to achieve stirring. With the dosing system, the required reagents can be quantitatively added into the container tank 6 during preparation, by storing the required reagents in the reagent tanks 9.

With the control system, the controller sends a control command to the temperature control output system 22 of the incubator 1 through a temperature signal of the temperature sensor 18, so that the temperature in the incubator 1 can always satisfy preparation requirements. The motor drive circuit 19 can control the motor 5 to switch on/switch off, and also can control the rotation rate and rotation time etc. The control module I 20 controls the drive device to move up and down, to stir the solution or centrifuge the solution if desired. The PH sensor 16 sends the signal of measured PH value of the reagent to the controller 17 in real time. The controller 17 controls the action of the control valve I 12 and controls the action of the driving mechanism via the control module II 21, to add reagents into the container tank 6 or to stop adding reagents into the container tank 6, so as to ensure that the PH value of the reagent eventually falls into the predetermined range, to precisely control PH value.

In view of above, the injectable tissue engineered cartilage in vitro construction apparatus of this embodiment is able to automatically perform in vitro construction of the injectable tissue engineered cartilage, to relief the burden of the medical staff and to improve production efficiency. Also, the quality of the resulting injectable tissue engineered cartilage can be guaranteed.

In particular, a method for in vitro constructing an injectable tissue engineered cartilage using the injectable tissue engineered cartilage in vitro construction apparatus of this embodiment is provided as follows:

1) Setting the temperature in the incubator to 0-4° C., placing 20 mg/ml of quantitative and seal-packed collagen-hydrochloric acid solution into the container tank 6, and placing 1.5 mol/L NaOH solution and centrifuged BMSCs solution into respective reagent tanks 9;

2) controlling the upper base 7 to move downward to allow the stirring rod 8 to go deep into the container; controlling the centrifuge to slowly rotate at a predetermined speed; controlling the control valve I 12 associated with the reagent tank 9 containing 1.5 mol/L NaOH solution to turn on; and controlling the piston rod 10 in the reagent tank 9 to move, to inject 1.5 mol/L NaOH solution into the container tank 6, to neutralize the collagen-hydrochloric acid solution; the PH sensor 16 transmitting a signal of the measured PH value of the solution in the container tank 6 to the controller 17 in real time, the controller 17 then sends a control command to the driving mechanism via control module II 21; when the PH value of the solution falls within the predetermined range of 0.2-7.5, the driving mechanism will be stopped and the associated control valve I 12 will be closed; upon neutralization, the solution has an ion concentration that matches saline; just to be sure, a displacement sensor 28 is further arranged in the reagent tank 9, to measure the amount of the reagents injected into the container tank 6.

3) controlling the control valve I 12 associated with the reagent tank 9 containing BMSCs solution to turn on; injecting quantitative BMSCs solution into the container tank 6; upon stirring well and having the stirring rod 7 to exit from the container, controlling the centrifuge to rotate at high speed to centrifugally remove bubbles and to obtain injectable tissue engineered cartilage. The injectable tissue engineered cartilage will be gelatinized under certain temperature, to repair cartilage injuries.

4) controlling the upper base 7 to move upward to allow the stirring rod 8 to exit out of the container tank 6; turning on the control valve II 15 and controlling the centrifuge to rotate at high speed; using centrifugal force to inject the injectable tissue engineered cartilage into the aseptic injector 13 for use.

In addition, a method for preparing the collagen-hydrochloric acid solution is as follows:

1) Under room temperature and sterile condition, cutting a knee joint cartilage from a fresh swine thighbone with a surgical knife, and temporarily storing the obtained knee joint cartilage in saline;

2) placing the cleaned cartilage slice in a low temperature freeze dryer for freeze-drying, using a low temperature pulverizer for smashing after moisture is fully removed, and weighing the cartilage microparticles;

3) placing the smashed cartilage in a container and injecting 75% medical alcohol with a volume that is 5 times the volume of the cartilage into the container; disinfecting the smashed cartilage for 24 h under 4° C. and sterile environment, and then using the centrifuge to centrifuge the solution at a speed of 8000 rpm for 20 min; removing the supernatant after precipitation, and using double distilled water to fully wash the retained precipitate;

4) injecting 4 mol/L guanidine hydrochloride solution with a volume that is 10 times the volume of the precipitate obtained from step 3) into the container; mixing and suspending the precipitate and the guanidine hydrochloride solution to obtain a suspension; stirring the suspension for 24 h, using the centrifuge to centrifuge the suspension at a speed of 8000 rpm for 20 min; removing the supernatant upon precipitation, and using 0.05 mol/L Tris-HCl buffer and 0.5 mol/L glacial acetic acid to fully wash the retained precipitate;

5) injecting 1 g/L pepsin-glacial acetic acid digest solution with a volume that is 5 times the volume of the precipitate obtained from step 4) into the container; stirring the resulting solution for 48 h; using the centrifuge to centrifuge the solution at a speed of 8000 rpm for 20 min; collecting supernatant upon precipitation; in which digest solution can be continuously added into the precipitate for digestion for 24 h and then removing supernatant;

6) injecting 2 mol/L NaOH into the container to quickly adjust PH value of the solution to 7.5; adding NaCl to allow the resulting solution to have a final concentration of 3 mol/L; salting out overnight under 4° C. and sterile environment; using the centrifuge to centrifuge the solution at a speed of 8000 rpm for 20 min; removing the supernatant upon precipitation, and retaining the precipitate;

7) continuously injecting triple distilled water into the container for dialyzing; centrifuging the solution for 20 min at a speed of 8000 rpm; and retaining precipitate, to obtain collagen;

8) weighing and quantifying, sterility testing, protein electrophoresing and amino acid analyzing the extracted collagen;

9) upon verifying that the resulting collagen is sterile, dissolving the resulting collagen in 0.15 mol/L HCl, to obtain collagen hydrochloric acid solution with a concentration of 20 mg/ml, and then seal-packed in tube for storing.

BMSCs solution can be prepared with existing methods, and thus no detailed description will be given.

The above preferred embodiments are intended to illustrate and not intended to limit the present invention. Although detailed description is provided to the present invention by way of the above preferred embodiments, it is understood that various modifications can be made in terms of form and details, without departing from the scope of the appended claims.

The invention claimed is:

1. An injectable tissue engineered cartilage in vitro construction apparatus, comprising:
an incubator;
a centrifugal device arranged in the incubator; and
a control system, for controlling a temperature in the incubator and an action of the centrifugal device;
wherein the centrifugal device comprises a centrifuge, a container base mounted on the centrifuge, a dosing system for adding preparation reagent, and a stirring system for stirring the reagent;
wherein the centrifuge comprises a bottom base and a rotatable plate cooperated with the container base; the bottom base has a motor for driving the rotatable plate to rotate;
wherein the container base has a container tank thereon; the stirring system comprises an upper base positioned above the container base; the upper base has a stirring rod aligned with the container tank extending from the bottom of the upper base; and, a driving device is arranged between the upper base and the bottom base for driving the upper base to move up and down;
wherein the dosing system comprises a reagent tank on top surface of the upper base for containing preparation reagent, a piston rod cooperated with the reagent tank, and a driving mechanism for driving the piston rod to move; a dosing channel is arranged between the reagent tank and the container tank, with a control valve I arranged thereon;
wherein the container base has a receiving device, which comprises an aseptic injector fixing in the container base; a receiving channel is arranged between the aseptic injector and the container tank with a control valve II arranged thereon;
wherein the container tank has a PH sensor for detecting PH value of the reagent; and
wherein the control system includes a controller, a timer connected with the controller for counting time, a temperature sensor for measuring the temperature in the incubator, a motor drive circuit for controlling an action of the motor, a control module I for controlling the driving device to move up and down, and a control module II for controlling an action of the driving mechanism; wherein the incubator is provided with a temperature control output system therein; the controller is respectively connected with the PH sensor, the control valve I, the control valve II and the temperature control output system; the controller receives a signal of PH value of the reagent measured by the PH sensor and sends a control command to the control module II and the control valve I.

2. The injectable tissue engineered cartilage in vitro construction apparatus according to claim 1, wherein: the driving device comprises a guiding rod arranged between the upper base and the bottom base and a cylinder for driving the guiding rod to perform fore and aft motion; wherein an electromagnetic directional valve is arranged on a gas path of the cylinder, and the control module I is connected with the electromagnetic directional valve.

3. The injectable tissue engineered cartilage in vitro construction apparatus according to claim 1, wherein: the dosing channel comprises dosing channels I arranged in the upper base corresponding to respective reagent tanks, and dosing channels II arranged in the stirring rod and respectively connected with the dosing channels I.

4. The injectable tissue engineered cartilage in vitro construction apparatus according to claim 3, wherein: the control valve I is arranged on the dosing channels I.

5. The injectable tissue engineered cartilage in vitro construction apparatus according to claim 1, wherein: the driving mechanism comprises a servo motor, a screw rod rotating under driven by the servo motor and in parallel with the piston rod, and a screw sleeve sleeved onto the screw rod, wherein the screw sleeve and the piston rod are fixedly connected, and the control module II is connected with the servo motor.

6. The injectable tissue engineered cartilage in vitro construction apparatus according to claim 1, wherein: the stirring rod has a stirring blade thereon.

7. The injectable tissue engineered cartilage in vitro construction apparatus according to claim 1, wherein: the reagent tank is provided with a displacement sensor for detecting position of the piston rod.

\* \* \* \* \*